(12) United States Patent
Cantournet et al.

(10) Patent No.: US 9,180,000 B2
(45) Date of Patent: Nov. 10, 2015

(54) DEVICE FOR TISSUE REPAIR

(75) Inventors: Sabine Cantournet, Vanves (FR); Laurent Corte, Paris (FR); Fabrice Detrez, Paris (FR); David N. Ku, Decatur, GA (US); Mohammed Cherkaoui, Marange Silvange (FR); Frances Baxter, Metz (FR); Jason Bach, Metz (FR)

(73) Assignees: CENTRE NATIONAL DE LA RECHERCHE SCIENTIFIQUE, Paris (FR); ASSOCIATION POUR LA RECHERCHE ET LE DEVELOPPEMENT DE METHODES ET PROCESSUS INDUSTRIELS "ARMINES", Paris (FR); GEORGIA TECH RESEARCH CORPORATION—GEORGIA INSTITUTE OF TECHNOLOGY, Atlanta, GA (US)

( * ) Notice: Subject to any disclaimer, the term of this patent is extended or adjusted under 35 U.S.C. 154(b) by 0 days.

(21) Appl. No.: 13/980,925

(22) PCT Filed: Jan. 20, 2012

(86) PCT No.: PCT/EP2012/050917
§ 371 (c)(1),
(2), (4) Date: Oct. 7, 2013

(87) PCT Pub. No.: WO2012/098251
PCT Pub. Date: Jul. 26, 2012

(65) Prior Publication Data
US 2014/0039620 A1    Feb. 6, 2014

(30) Foreign Application Priority Data

Jan. 20, 2011    (WO) .................. PCT/IB2011/000312

(51) Int. Cl.
*A61F 2/08*    (2006.01)

(52) U.S. Cl.
CPC ........... *A61F 2/08* (2013.01); *A61F 2250/0018* (2013.01)

(58) Field of Classification Search
CPC .............. A61F 2/02; A61F 2/08; A61F 2/28; A61L 27/48
USPC .............................. 623/13.1–13.11
See application file for complete search history.

(56) References Cited

U.S. PATENT DOCUMENTS

| | | | |
|---|---|---|---|
| 5,800,543 A | 9/1998 | McLeod et al. | |
| 5,981,826 A | 11/1999 | Ku et al. | |
| 6,610,064 B1 * | 8/2003 | Goble et al. | 606/232 |

(Continued)

FOREIGN PATENT DOCUMENTS

| | | |
|---|---|---|
| EP | 1 493 404 | 1/2005 |
| FR | 2 700 111 | 7/1994 |

(Continued)

OTHER PUBLICATIONS

International Search Report dated Mar. 6, 2012, corresponding to PCT/EP2012/050917.

*Primary Examiner* — Suzette J Gherbi
(74) *Attorney, Agent, or Firm* — Young & Thompson

(57) ABSTRACT

A based device for use as tissue repair includes a median part between two end parts. The median and end parts have a different tensile stiffness.

26 Claims, 5 Drawing Sheets

(56) References Cited

U.S. PATENT DOCUMENTS

| | | |
|---|---|---|
| 6,986,771 B2 * 1/2006 | Paul et al. | 606/254 |
| 2003/0114929 A1 6/2003 | Knudsen et al. | |
| 2004/0018226 A1 1/2004 | Wnek et al. | |
| 2007/0134333 A1 6/2007 | Thomas et al. | |
| 2009/0305024 A1 12/2009 | Gvozdic | |
| 2011/0288199 A1 * 11/2011 | Lowman et al. | 523/114 |
| 2013/0032059 A1 * 2/2013 | Trexler et al. | 106/164.01 |

FOREIGN PATENT DOCUMENTS

| | | |
|---|---|---|
| JP | 4141178 | 8/2008 |
| WO | 98/22046 | 5/1998 |
| WO | 01/17574 | 3/2001 |
| WO | 2006/102756 | 10/2006 |
| WO | 2009/047767 | 4/2009 |
| WO | 2009/113076 | 9/2009 |
| WO | 2010/014446 | 2/2010 |

* cited by examiner

DEVICE FOR TISSUE REPAIR

FIELD OF THE INVENTION

The present invention relates to a hydrogel based device for use as tissue repair.

BACKGROUND OF THE INVENTION

Hundreds of thousands of anterior cruciate ligaments (ACL) are torn every year and this trend has been increasing with the rise of participation in sports in the general population and in particular in females and older participants. For young and/or athletic active individuals the standard care is based on ligament reconstruction. Several replacement tissues can be envisaged using either grafts (auto, allo and xeno) or artificial materials. Xenografts, ligaments from other animals, and allografts from cadaveric human tissue are possibilities that overcome the need to autologous tissues and avoid the risk of donor-site morbidity. However, their use poses several issues including risks of disease transmission, graft rejection and inflammation. Moreover, in the case of allografts, the supply is so small that the market demand can never be met from this source. Autograft tissues extracted from the patellar tendon, quadriceps tendon-patellar bone or the hamstring tendons are currently the most common sources of grafts for ACL reconstruction. Yet this therapy relies on the extraction of healthy tissue which implies risks of donor-site morbidity, an initial low strength, a high probability of rupture at the initial stages and a long and painful recovery period. The use of artificial prosthetic ligaments as an alternative to autografts could bring substantial improvements in the existing reconstruction therapies.

Several prosthetic devices for ACL replacement have been made over the past thirty years using a wide range of materials. The materials which have been considered for these devices including polyester (Stryker Dacron® ligament prosthesis, Leeds-Keio), polytetrafluoroethylene and fluoropolymers (Gore-Tex®), carbon fibers, polyethylene, nylon and polystyrene. However none of these artificial ligaments have demonstrated positive long term results in vivo. Failures of previous devices mostly originate from mechanical failures or from a lack of biocompatibility. Mechanical failures include i) rupture caused by wear, fatigue or severe loading in the knee and ii) laxity in the joint after creep of the prosthetic ligament or loosening of the fixation element in the bone. Biocompatibility issues primarily manifest as immunogenic particulation leading to chronic synovitis. Due to high incidence of such problems, most if not all the previous artificial ligaments have been withdrawn from the commercial market. For example, no such devices are currently approved for clinical use by the Food and Drug Administration of the United States of America (FDA).

Over the last decades, statistics have been collected that confirm the poor long term efficacy of existing artificial ligaments. A study of 855 artificial cruciate ligaments over a 15-year period found that there was 40-78% failure rate (Fu F. H. et al. American Journal of Sports Medicine, 2000, 28(1), 124-130). Another report found that around 80% of knees which had been reconstructed using Dacron prosthetic ligaments had developed significant osteoarthritic symptoms at a 9 year follow up (Fu F. H. cited above). Similarly, a study of 268 patients revealed that Gore-Tex® anterior cruciate ligament prosthesis yielded a failure rate of 42% with case of effusions, rupture and strong loosening (George M. S. et al, American Journal of Sports Medicine, 2006, 34(12), 2026-2037). Overall, complication rates for artificial ligament operations are of the order of 40-50%, which is much higher than the rate with autologous and allogenic ligaments.

As an alternative to non-biodegradable artificial ligaments, research efforts are being carried out to develop tissue engineered (TE) ligaments for which a biodegradable scaffold first replaces the native ligament and is progressively replaced by a new reconstructed living tissue. Several systems have recently been designed using silk, collagen or polylactic acid biodegradable fibers (Freeman J. W. et al. Journal of Biomechanics, 2010, doi: 10.1016/j.biomech.2010.10.043). Nevertheless, the management of cell sourcing as well as the control of scaffold degradation while ensuring proper mechanical properties remain unsolved issues that still need to be addressed before clinical use.

Most of the patents deal with the methods of attachment or fixation design to attach an artificial ligament to the bones of a joint. Recent examples are given below.

FR 2 700 111 relates to an artificial ligament consisting of a fixed section and a moving sleeve which form two separate ligaments of the same or different lengths, joined together so that they can slide relative to one another. The two ligaments can be made from plaited, woven or knitted fibres of the same or different materials, with their ends joined together by a thermo-shrink material or a supple adhesive. The outer ligament can be made with sections of reduced resistance which allow its length to be varied. The ligaments can be made from Dacron® (RTM) or other synthetic fibres, or from natural cellulose fibres which are treated to make them biocompatible.

US 2003/114929 discloses a prosthetic ligament including a cord of thermotropic liquid crystal filaments. Preferably the cord is a string or thin rope made by several strands braided, twisted, or woven together. Strands are, preferably, made of a multi-filament thread.

U.S. Pat. No. 5,800,543 relates to an artificial ligament device comprising a plurality of tows of biocompatible material (for example polyester) secured side-by-side in a flat elongate array by braiding, the tows being looped back at one end of the device to form an eye, the flat lengths adjoining the eye being secured to each other side-by-side by stitching, the tows around the eye being grouped together and whipped, and lashing being applied around a base of the eye.

WO 2009/047767 provides a ligament prosthesis having a first end and a second end, comprising a first load bearing element and a second load bearing element, the first and second load bearing elements differing in one or more mechanical properties and being arranged in the prosthesis in series. The load bearing elements may be made from an alloy and, in order to protect nearby organs and tissues from abrasion from the prosthesis and vice versa, may be contained in a sleeve made from biodegradable polymers such as poliglecaprone, polyglycolic acid, polylactic acid, polydioxanone, or co-polymers of the aforementioned polymers.

WO 2009/113076 provides a ligament prosthesis having an undeployed configuration and a deployed configuration. The prosthesis has a resistance to tension in the undeployed configuration that is less than its resistance to tension in the deployed configuration. In the deployed configuration, the prosthesis is capable of twisting and bending. In one embodiment, the prosthesis has a meshwork of filaments woven, knitted or braided into a slender cylinder. The prosthesis may be used to replace an anterior or posterior cruciate ligament.

WO 98/22046 discloses a "free strand" ligament that is naturally self-convoluted between the two ends of the intra-articular median part.

With the foregoing disadvantages of the prior art in mind, it appears that there is a need for a device which i) is biocompatible on the short and long term, meaning after years of implantation in vivo, ii) reproduces closely the non-linear elastic mechanical behaviour of native ligaments and tendons including the stiffness and the toe-region, iii) ensures ultimate tensile stress (strength) and ultimate tensile strain that are safe with respect to the patient's activity. Polymer hydrogels constitute relevant materials in that respect.

Hydrogels, also called aquagels, are hydrophilic polymer networks that can absorb water and swell without dissolving at least temporarily. Depending on the physico-chemical properties of these networks, levels of water absorption can vary greatly from about 10% to thousand times their dry weight. An important characteristic of hydrogels is that they can possess a water content and a molecular structure very similar to those of living tissues. These features confer them biocompatibility, lubricity, rubbery elasticity and possibly biodegradability, which are of interest for biomedical applications and more particularly tissue replacement. Examples of hydrogel forming polymers that are relevant for biomedical applications are polyvinyl alcohol, polyethylene-glycol, polysaccharides, polylactic acids and their copolymers U.S. Pat. No. 5,981,826 provides a poly(vinyl alcohol) hydrogel construct having a wide range of mechanical strengths for use as a human tissue replacement. It may be especially useful in surgical and other medical applications as an artificial material for replacing and reconstructing soft tissues in humans and other mammals. Soft tissue body parts which can be replaced or reconstructed by the hydrogel include vascular grafts, heart valves, esophageal tissue, skin, corneal tissue, cartilage, meniscus, and tendon. However, the reported tensile modulus of elasticity for the so-prepared material is less than 1 MPa, which is too low as compared to the ultimate tensile stress of ligaments and tendons, which is greater than 100 MPa.

WO/2006/102756 relates to a hydrogel exhibiting anisotropic properties which is poly(vinyl alcohol) produced by preparing a solution of poly(vinyl alcohol) with a pre-selected concentration, thermally cycling the solution by freezing and thawing, stretching the hydrogel and thermally cycling the hydrogel at least one more time. Said anisotropic hydrogel is used for soft tissue replacement selected from vascular vessels, coronary arteries, heart valve leaflets, heart valve stent, cartilage, ligaments and skin. However, the ultimate tensile stress for the so-prepared materials do not exceed 0.4 MPa, which is too low as compared to the ultimate tensile stress of ligaments and tendons, estimated in the range 30-50 MPa.

WO/2001/017574 discloses a hydrogel intended for orthopedic applications wherein the tissue is selected from the group consisting of bone, cartilage, meniscus, bursa, synovial membranes, tendons, ligaments, muscle and vertebral disks. Like for WO/2006/102756, the ultimate tensile stress for the preferred material is about 8 MPa, which is too low for the replacement of most ligaments and tendons.

JP4141178 discloses an artificial tendon and an artificial ligament consisting of polyvinyl alcohol fiber with a tensile strength of 12 g/d or larger and a tensile breaking elongation of 6% or smaller which is much less than the devices of the present invention A non-biodegradable device that can be installed in-vivo to repair a ligament or tendon, that is biocompatible and that reproduces closely the mechanical properties of native ligaments and tendons as well as ensures the appropriate values of tensile strength and ultimate tensile strain required for ligament or tendon replacement is needed.

DESCRIPTION OF THE INVENTION

The inventors propose a novel type of device, in particular an artificial ligament or tendon which can be placed and fixed in a patient at the location of respectively a ligament or a tendon and which is made of biocompatible hydrogel and reproduces closely the tensile mechanical response of native ligaments or tendon with values of ultimate tensile stress and ultimate tensile strain that are appropriate for ligament or tendon repair. It can be placed in the patient using minimally invasive techniques. Unlike autograft techniques, this device does not necessitate the sacrifice of healthy tendons or ligaments from the patient.

Thus an object of the present invention is a biocompatible device in the form of an elongated body comprising at least a flexible median part between two end parts, said body having a fibrous structure formed from biocompatible hydrogel fibers, said hydrogel fibers being assembled to form the body of the device.

A further object of the present invention is a biocompatible device in the form of an elongated body comprising a flexible median part between two end parts showing a different tensile stiffness from that of the median part, said body having a fibrous structure formed from biocompatible hydrogel forming fibers, said hydrogel forming fibers forming the body of the device.

The words "terminal end parts" can also be used in place of "end parts" but the language "end parts" is preferred.

The words "hydrogel fibers", can also be used in place of "hydrogel forming fibers" but the language "hydrogel forming fibers" is preferred. The word "forming" can also be inserted in the terms "hydrogel matrix", "hydrogel polymers".

The words "continuous" and "threads" are synonymous.

According to the invention, the word "biocompatible" means that the hydrogel and the device elicit little or no immune response in a given organism, or is able to integrate with the tissue.

According to the invention, the word "fibrous" means that the body of the device contains at least 1% in weight of products of fibrous nature. Preferably, the body of the device contains at least 10% in weight of products of fibrous nature According to the invention the flexible median part reproduces the behavior of the natural ligament or tendon whereas at least one end part is designed to be fixed on a bone.

According to the invention, the body may be formed by any techniques known from the one skilled in the art, for example by simple assembly of the fibers keeping them individual, by assembly of the fibers into threads or strands, by braiding, by knitting or by weaving.

According to the invention, the device is advantageously an artificial ligament used for repairing any ligament in animals, in particular non human mammals or humans. Ligaments which may be repaired may be selected from the followings: head and neck ligaments (cricothyroid ligament, periodontal ligament, suspensory ligament of the lens), wrist ligaments (palmar radiocarpal ligament, dorsal radiocarpal ligament, ulnar collateral ligament, radial collateral ligament), shoulder ligament (rotator cuff), knee ligament (anterior cruciate ligament (ACL), lateral collateral ligament (LCL), posterior cruciate ligament (PCL), medial collateral ligament (MCL), cranial cruciate ligament (CrCL)—quadruped equivalent of ACL, caudal cruciate ligament (CaCL)—quadruped equivalent of PCL, patellar ligament).

Anterior cruciate ligament (ACL) is the most likely ligament to be replaced by the device of the invention.

A further object of the present invention is a device wherein the two end parts show a higher tensile stiffness than that of the flexible median part.

Another object of the present invention is a device wherein the two end parts show a higher bending stiffness than that of the flexible median part.

A further object of the present invention is a device wherein the median part shows an ultimate tensile strain greater than 6%, advantageously from 6 to 100%, more advantageously from 10 to 80%.

A further object of the present invention is a device wherein the two end parts show a tensile stiffness that is from 10% to 100 times in particular 10%, 50%, 2 or 5 times higher, than that of the flexible median part.

A further object of the present invention is a device wherein the end parts are placed adjacently to each of the ends of the median part and are made of swellable, porous and braided, twisted, woven or knitted sections. The end parts sections may be permeable.

A further object of the present invention is a device wherein the swelling of the end parts is less than 40%, preferably less than 20% in weight and the porosity is greater than 1%.

The swelling of the device is measured according to standard procedures.

Swelling is the property of a device whereby the volume increases upon exposure to water.

Porosity is the property of a device whereby open spaces or pores exist without polymeric material. Cells can migrate into the spaces or pores contained in the device. Porosity is defined as the fraction of the volume of open spaces or pores over the total volume.

In some of the devices according to the invention, the flexible median part has a non linear elasticity.

The invention concerns more particularly a device having a median part whose tension stress-strain curve shows a low stiffness region at the lowest levels of tensile strain and a higher stiffness region at greater levels of strain.

In some of the devices according to the invention, the flexible median part has a linear elasticity.

In an advantageous embodiment, the tensile strength and the ultimate tensile strain of the device defined above are measured after equilibration in water or bodily liquids, until weight is stable, typically a few hours at 20° C. The same conditions also apply to the measure of the ultimate tensile load, tensile stiffness, tensile modulus and flexural modulus.

The device according to the invention shows a tensile strength between 10 and 200 MPa, advantageously between 15 and 50 MPa (corresponding to an ultimate load between 1100 and 4000N for a ligament with a diameter of 1 cm) and an ultimate tensile strain between 10 and 100%, advantageously 15-80%.

In an advantageous embodiment, the device according to the invention shows an ultimate tensile load between 30 and 60000N, advantageously comprised between 300 and 4000N and an ultimate tensile strain comprised between 10 and 100%, advantageously between 15 and 80%.

Another aspect of the invention concerns a device as defined above showing a tensile strength greater than 10 MPa, advantageously comprised from 15 to 50 MPa.

A device according to the invention can advantageously show in the 0 to 5% strain range a tensile modulus of 1 to 500 MPa in particular 1 to 10, 10 to 40, 40 to 100, 100 to 150, 150 to 300, 300 to 500 MPa.

A device according to the invention can also advantageously show in the 10 to 15%. strain range a tensile modulus 1 to 500 MPa in particular 1 to 10, 10 to 40, 40 to 100, 100 to 150, 150 to 300, 300 to 500 MPa A device according to the invention wherein the median part shows in the 10 to 15% strain range a tensile stiffness comprised from about 10 to 500 N/%, preferably from about 20 to about 300 N/%.

A device according to the invention can advantageously show an ultimate tensile load greater than 30 N advantageously comprised between 300 and 4000N A device according to the invention can advantageously show a bending stiffness from 10 to 100 MPa.

A device according to the invention wherein the median part shows a flexural modulus from 0.1 to 200 MPa advantageously comprised between 1 and 100 MPa.

According to the invention, the device is advantageously made of continuous fibers. The threads used to make the device can also be continuous.

By continuous fibers it is meant that the fibers are prolonged and span from one end of the device to the other end without interruption. Preferably, a type of fiber that covers the entire dimension of a part without a break or interruption is used.

In an advantageous embodiment of the invention, the central core of the device is made of a bundle of parallel or twisted threads.

In a preferred embodiment of the invention, a device according to the invention has end parts that are made of tubular braided, twisted, woven or knitted sections that contain at least one osseointegration promoting substance and/or has holes at each end of the tubular section or on the side of it to allow injection of materials into the space inside the tube.

A device according to the invention has end parts that are coated or impregnated with one or several osseointegration-promoting substances, preferably calcium phosphate and/or calcium sulfate.

A device according to the invention is characterized in that at least one of the end parts is filled with a substance, preferably bone mulch or bone cement or a mineral filler preferably a bioactive glass or hydroxyapatite.

The term bioactive glass is well known in the art. These materials usually contain Ca-phosphates and or Ca-sulphates. CaO, $P_2O_5$, $SiO_2$ and $Na_2O$ are typical constituents for bio elements.

Examples of commercially available materials contain:

46.1 mol % $SiO_2$, 26.9 mol % CaO, 24.4 mol % $Na_2O$ and 2.5 mol % $P_2O_5$. Bioglass 60 mol % $SiO_2$, 36 mol % CaO and 4 mol % $P_2O_5$.

70 mol % $SiO_2$, 30 mol % CaO.

Other biocompatible materials like porcelain, alumina, zirconia can also be used.

In a preferred embodiment of the invention, device according to the invention, the hydrogel forming fibers are made of polyvinyl alcohol.

In a preferred embodiment of the invention, the hydrogel forming fibers are made of polyvinyl alcohol having a water absorption higher than 10% and preferably comprised between 10 and 80% in weight.

According to the invention any biocompatible hydrogel known from the one skilled in the art may be used if the moisture content is comprised between 10 and 80%. A suitable hydrogel is, for example, the PVA hydrogels disclosed in U.S. Pat. No. 5,981,826, or sold by Salumedica LLC. Commercial hydrogel forming fibers can be used like PVA fibers Solvron® sold by Nitivy Company Ltd.

Preferably, the hydrogel forming fibers are made of polyvinyl alcohol fibers having a linear mass density of $8 \cdot 10^{-5}$ to 2500 deniers preferably 45 deniers and a tensile strength greater than 10 g/d preferably 44 g/d.

Fibers having a diameter of 0.1 to 1 µm made by electrospinning or fibers having a diameter from 1 to 500 µm made by conventional methods can be used. It is well in the knowledge of the one skilled in the art to adjust the number of fibers or threads to the size and density of the fibers. For instance, if very fine fibers like those obtained by electrospinning (typically on the micro or nano scale) are used the skilled artisan will use many more fibers to make the device according to the invention.

In an advantageous embodiment according to the invention, the fibrous structure may also contain other type of biocompatible fibers assembled with the hydrogel fibers, for example biocompatible carbon fibers or metal fibers like titanium and titanium alloy fibers or polymeric fibers selected from the group consisting of polyethylene (PE), polypropylene (PP), polyamides (PA), polycarbonates (PC), polyurethanes (PU), polyurethane urea, polyesters like polyethylene terephtalate (PET), polyfluoropolymers like polytetrafluoroethylene (PTFE), polyacrylates like polymethyl methacrylate (PMMA), polyethylene glycol (PEG), poly-L-lactic acid (PLLA), poly-G-lactic acid (PGLA), poly-caprolactone (PCL), polyglycolide, polysaccharides like cellulose, hyaluronic acid, proteins like elastin, silk, collagen and from blends or copolymers obtained with polymers from this group.

More preferably, the fibrous structure may also contain other types of biocompatible fibers assembled with the hydrogel fibers, for example fibers made in one or several of the following polymers can be used: Polyethylene (PE), Poly-L-lactic acid (PLLA), Poly-G-lactic acid (PGLA), Poly-caprolactone (PCL), Silk, Polyesters, Polyethylene terephtalate (PET), Polytetrafluoroethylene (PTFE), PLGA, Ti wires fibers assembled with the hydrogel forming fibers.

A device according to the invention is characterized in that the body is partly or totally coated or entrapped in a hydrogel matrix.

According to the invention, the diameter of the device is similar to the one of the natural part to be repaired; for example in the case of an artificial ligament for repairing a human knee ligament the diameter of the device is between 2 mm and 2 cm, advantageously comprised between 5 and 10 mm. The length of the body is also similar to the one of the natural ligament. For the case of the human knee ligament, it is between 0.5 and 5 cm and the length of the whole ligament comprising the median part and the end parts is between 5 and 25 cm, advantageously between 10 and 20 cm, more advantageously is equal to about 15 cm. The choice of the diameter and of the length of the device is well in the hand of the one skilled in the art who may adapt said parameters to the type of ligament or tendon he wishes to repair.

According to the invention, the device may further contain anchoring systems at least at one end part which may be any system known from the one skilled in the art, like for example a hook, a screw, a buckle, a bone anchor, an interference screw, a cross pin or a suture button. It may also be an eye spliced at said end of the device.

In an advantageous embodiment according to the invention, either the fibers, or the assembly of fibers (threads, strands, braid, knit fabric or woven fabric) or the whole body or both of them or the three are entrapped in a hydrogel matrix or coated by a hydrogel, said hydrogel being the same or being different from the hydrogel used for the fibers. Said coating or matrix may contain mineral fillers imparting better anchoring on the bone like calcium phosphates (hydroxyapatite and the like) or may be swollen by water in situ in order to have better anchoring on the bone.

Then in an advantageous embodiment of the invention, the anchoring system may be the hydrogel coated or embedded end parts of the device themselves.

It is to be noted that the terms embedded and entrapped are usually synonymous.

Where coating by a hydrogel or embedding in a hydrogel matrix is performed on the fibers or strands, then it is performed prior to assembly of the body. Said matrix or coating plays several roles:
  i) It better redeploys the efforts between fibers
  ii) It lubricates the contact between the device and surrounding tissues thus diminishing the risks of inflammation and of failure by wear,
  iii) It provides additional stiffness to the end parts in order to reduce deformation in the bone tunnels and favor adhesion with bone.
  iv) According to the properties of the hydrogel, it is used either to prevent cellular adhesion on the median part of the body or to reinforce the bone-device interface and accelerates the osseous integration of the end parts.

The device may have any form suitable for repairing the corresponding natural part. It is generally elongated in shape and the anchoring system at at least one end of the device is adapted for attachment to a musculo-skeletal tissue such as bone.

In an advantageous embodiment of the invention, the device has three parts: a central part and two extreme parts. In the case of a cruciate ligament the extreme parts are called respectively tibial and femoral part and the central part is called ligamentous part.

In an advantageous embodiment according to the invention, the fibers may be assembled to threads, and the strands are strands of threads. The strands may be twisted in the opposite direction of the twist of the threads to gain a greater stiffness and cohesion of the structure.

In another advantageous embodiment, the strands may surround a hollow core. The obtained structure has several roles:
  i) The hollow core provides a lower resistance to bending and thus a greater flexibility to the central part.
  ii) The hollow core can be filled by a substance like bone cement or bone mulch or an appropriate fixation device like interference screws to better fix one or both of the extreme parts, tibial and femoral parts in the case of knee ligaments.

In another advantageous embodiment of the invention, the fibers are oriented in a direction of loading of the prosthetic ligament.

In another advantageous embodiment of the invention, the fibers may be assembled to threads, and the threads are oriented in a direction of loading of the prosthetic ligament.

In another advantageous embodiment the assembly pattern can be different for each part. For example, where the fibers are assembled into strands, strands can be twisted in the central part and braided in the end-parts.

The fibers themselves or the coating or both may contain at least one compound selected from the group consisting of growth factors, drugs like anti-inflammatory drugs or a mineral filler like calcium phosphates (hydroxyapatite and the like).

In an advantageous embodiment, the stiffness of the device of the invention is comprised from about 10 to 500 N/%, preferably from about 20 to about 300 N/%.

Typical devices for ACL replacement that can be prepared according to the present invention contain 16 polyvinyl alcohol strands that can be assembled parallel to the direction of loading or consist in 4 twisted ropes each consisting of 4 PVA strands twisted together. Another type of device is made of 22

PVA strands consisting in 4 braided PVA strands surrounded by 6 twisted ropes each consisting of 3 PVA strands twisted together. Alternatively up to 27 UHMWPE threads can be substituted for some of the PVA strands.

The annealing step can preferably be performed at a temperature comprised between 130 and 190° for 10 minutes to one hour.

Practical intermediates materials for preparing devices according to the invention are disclosed thereafter. These intermediates are then treated to differentiate the end parts and the median part. The end parts and median part of the device can be treated separately by the methods disclosed herewith.

1) 16 PVA (polyvinyl alcohol) strands assembled parallel to the direction of loading.
2) 16 PVA strands consisting of 4 twisted ropes each consisting of 4 PVA strands twisted together.
3) 22 PVA strands consisting of a Central core of 4 braided PVA strands surrounded by 6 twisted ropes each consisting of 3 PVA strands twisted together.
4) Same as the preceding device with 27 UHMWPE threads together as a unit substituted for one of the PVA strands in the braided central core (21 PVA strands and 27 UHMWPE threads in total)
5) 16 PVA strands assembled parallel to the direction of loading with annealing of the structure at 130° C. for 1 hour.
6) 16 PVA strands assembled parallel to the direction of loading with annealing of the structure at 160° C. for 1 hour.
7) 16 PVA strands assembled parallel to the direction of loading with annealing of the structure at 190° C. for 1 hour.
8) 16 PVA strands assembled parallel to the direction of loading with annealing of the structure at 160° C. for 10 minutes
9) 16 PVA strands assembled parallel to the direction of loading with annealing of the structure at 190° C. for 10 minutes
10) 16 PVA strands assembled parallel to the direction of loading with coating by PVA hydrogel using the immersion method and applying one freezing-thawing cycle.

The device according to the invention may be prepared by any process known from the one skilled in the art. The process shall permit the modification of each part of the body separately.

Consequently another object of the invention is a process for preparing a device according to the instant invention with steps comprising:
a) assembly of fibers to form the body,
b) impregnation of the fibers, the assembly of fibers or a part or the whole body of the device in a solution of hydrogel forming polymer or a solution of monomer or oligomer to coat said fibers, or said strands or said assembly of fibers or said body or to embed them in a hydrogel matrix, followed in the case of a solution of hydrogen forming monomer or oligomer by a polymerization step
c) physical or chemical cross-linking of the hydrogel coating, the hydrogel forming fibers or the hydrogel matrix of a part or the whole body of the device.

In the process, the order of steps a), b) and c) may be modified or one of step b) and c) may be deleted. For example where fibers or threads or strands are coated or embedded in hydrogel, step b) is performed before step a). Step c) may be provided directly on the hydrogel forming fibers before step a) or step b) may be performed before step a).

Cross-linking in step c) may be performed by any techniques known in the art. Suitable techniques include application of heat and/or irradiation like UV or gamma rays and/or chemicals like dialdehydes in the case of PVA hydrogels and/or freezing/thawing or drying/rehydrating cycles.

In a preferred embodiment of the process in the case where polyvinyl alcohol fibers are used, step c) comprises a physical cross-linking step selected from a series of freezing/thawing cycles and/or drying/rehydrating cycles and/or a chemical cross-linking step preferably using irradiation and/or a dialdehyde cross-linker preferably glutaraldehyde In a further embodiment of the process according to the invention, the assembly of fibers of step a) is performed around a rod to form a hollow In a third embodiment of the process according to the invention, it further comprises an annealing step of a part or the whole body of the device above the glass transition temperature of the hydrogel forming polymer and below the dissociation temperature of the hydrogel network. In the case of polyvinyl alcohol, the temperature of the said step is preferably in the range between 100° C. to 200° C. Said annealing step may be performed directly on the fibers prior to step a) or before or after step c).

The process according to the invention the annealing step can also be performed at a temperature near the melting point of the hydrogel forming fibers, before or after step c) on a part or the whole body of the device In a preferred embodiment of the process, the device is maintained under tension during annealing.

According to the invention, it is possible, in the process, to treat differently and separately the end-parts and median parts in order to have condign properties for each part.

The device according to the invention may be used as ligament or tendon including elbow, shoulder, ankle, knee in dog, horse or human, in particular a cruciate ligament, more particularly an anterior cruciate ligament and may be configured therefore.

Consequently another object of the instant invention is a method for inserting a device comprising the following steps:
a. providing a device according to the instant invention
b. insertion of the device in the replacement site
c. attaching a first end of said device to a first attachment site
d. possibly, pretensioning the device
e. attaching the second end of the device to a second attachment site.

The first and the second attachment sites may be any musculo-skeletal tissue to which the natural ligament or tendon is attached in a human or non-human animal. In case of the anterior cruciate ligament if the first attachment site is the femur then the second attachment site is the tibia. If the first attachment site is the tibia then the second attachment site is the femur.

In order to understand the invention and to see how it may be carried out in practice, embodiments will now be described by way of examples and drawings.

FIG. 1 is a schematic drawing of one embodiment according to the invention. About 15 hydrogel threads (1) constituted from about 12 hydrogel continuous fibers are assembled to form a strand (2). Several strands, which number is adjusted to impart the good mechanical properties, are assembled to form the body (3), about 9 to 25 strands can be used for replacement of a human ACL. The fiber assembly may be designed to have a hollow core (7). Strands may be embedded in a hydrogel matrix which is of the same nature as the fibers. The tibial part (5) and the femoral part (6) or both may be coated by a hydrogel matrix (8) differently from the ligamentous part (median part) (4). On this particular design, the anchoring system (9) is a loop spliced at one end of the device.

FIG. 2 illustrates the load versus strain response during a tensile test for several types of device obtained following the invention. These results are compared to the tensile behavior of real ligaments and tendons as reported in the literature (Woo S. L. et al. American Journal of Sports Medicine, 1991, 19, p. 217; Kim D. H. et al. American Journal of Sports Medicine, 2003, 31, p. 861.).

EXAMPLE 1

Device Design

Figure 1:
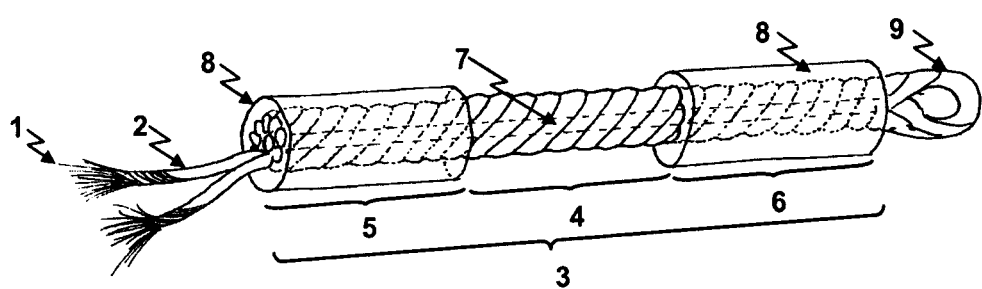

Several devices have been prepared from the assembly of PVA fibers only, or PVA fibers and ultra-high molecular weight polyethylene (UHMWPE) fibers.

PVA fibers (suitably with a dissolution temperature greater than 50° C. and 95+% hydrolyzed) were obtained as threads of more than 600 dtex composed of several continuous fibers like the Solvron® MH675 from Nitivy Company Ltd. PVA strands were prepared by winding 15 PVA threads together. UHMWPE fibers were obtained as threads of more than 60 dtex like Dyneema® from DSM.

Ten types of assembly were created with various structures, PVA/UHMWPE compositions and treatments. Fiber assemblies were approximately 10 mm in diameter, which is approximately the same diameter as the native ligament of the knee and currently used grafts. Geometries, compositions and treatments are summarized in Table 1.

TABLE 1

| Sample | Components | Description |
| --- | --- | --- |
| Type 1 | 16 PVA strands | 16 PVA strands are assembled parallel to the direction of loading. |
| Type 2 | 16 PVA strands | 4 twisted ropes each consisting of 4 PVA strands twisted together. |
| Type 3 | 22 PVA strands | Central core of 4 braided PVA strands surrounded by 6 twisted ropes each consisting of 3 PVA strands twisted together. |
| Type 4 | 21 PVA strands 27 UHMWPE threads | Same as Type 3 but with 27 UHMWPE threads together as a unit substituted for one of the PVA strands in the braided central core. |
| Type 5 | 16 PVA strands | Same as Type 1 but with annealing of the structure at 130° C. for 1 hour. |
| Type 6 | 16 PVA strands | Same as Type 1 but with annealing of the structure at 160° C. for 1 hour. |
| Type 7 | 16 PVA strands | Same as Type 1 but with annealing of the structure at 190° C. for 1 hour. |
| Type 8 | 16 PVA strands | Same as Type 1 but with annealing of the structure at 160° C. for 10 min. |
| Type 9 | 16 PVA strands | Same as Type 1 but with annealing of the structure at 190° C. for 10 min. |
| Type 10 | 16 PVA strands | Same as Type 1 but with coating by PVA hydrogel using the immersion method and applying one freezing-thawing cycle. |

To illustrate the effect of annealing, Type 1 assemblies were annealed in an oven at several temperatures and during different annealing times (see Types 5-9) in Table 1. In a preferred method, fiber assemblies are maintained under tension during annealing by clamping them on a metal frame.

To embed or coat the device, a PVA solution with the desired concentration (suitably in the range 5-20 wt %) was prepared either by dissolving the PVA fibers or by dissolving another PVA like PVA sold by Sigma Aldrich (suitably with MW of 80,000 to 186,000, 99+% hydrolyzed). These PVA solutions were obtained in distilled water by mixing and heating for about 1 hour around 90° C.

In one method, fiber assemblies were mounted on a metallic frame, immersed for one day at 20° C. in the solution and removed from the solution. In another method, they were encased in cylindrical moulds and the PVA solution was poured in these same moulds. To cross-link the hydrogel solution, the devices obtained by these two methods were thermally cycled by freezing at about −18° C. for 12 hours, and then thawing in air or distilled water by heating back to 20° C. for 12 hours. This process represents one cycle by freezing-thawing. Up to 10 cycles have been applied. Cross-linking was also performed by drying the devices at 20° C. in ethanol for one day and then in vacuum for one day and by rehydrating them by immersion in distilled water for one day. This process represents one cycle by drying-rehydrating.

The end parts and median part of the device could be treated separately by these two methods. In the method by immersion, only the end-parts could be embedded in the PVA matrix by partially immersing the sample. In the method with moulds, separate moulds could be used for each end- and median parts. In a first step, PVA embedding was applied to the end-parts and followed by cross-linking and possibly annealing. A second PVA embedding was then applied to the median part only or to the entire device and followed by another cross-linking step. Different stiffnesses and properties for the median and end-parts were produced by varying the degree of cross-linking achieved during the first and second steps. In one method, a solution of PVA with a dispersion of hydroxyapatite was used to coat the end-parts only.

EXAMPLE 2

Properties of the Device

These results correspond to the fiber assembly types presented in Table 1.

1.1. Biocompatibility Testing 1H and 13C NMR analysis showed that there is no noticeable distinction between the PVA used for the hydrogel forming fibers and a biocompatible PVA already used for cartilage replacement like the one described in U.S. Pat. No. 5,981, 826. In particular, there are no detectable traces of other organic compounds and PVA is hydrolyzed over 98%. For this latter PVA, biocompatibility was qualified by testing for ability to produce cytotoxicity, intracutaneous irritation, sensitization by Kligman maximization, Ames mutagenicity, chromosomal aberration, and chronic toxicity. Chronic toxicity was assessed in combination with long-term subcutaneous implantation in a 13-week rat animal model. The material met the acceptance criteria for all testing conducted.

1.2 Dimensions

The diameter of the samples presented in Table 1 was measured and found in the range 10-11 mm 1.3. Tensile Properties 1.3.1. Measurement Hydrogel swelling was achieved by immersing fiber assemblies in distilled water at 23° C. for 24 h prior to testing. Tensile testing was performed on an Instron 5966 apparatus using capstan fixations. Samples were tested less than 5 min after removal of water and pulled at a strain rate of about $10^{-2} s^{-1}$ (1.5 mm s-1) which was fast enough to avoid any significant drying during testing. Testing was performed at 23° C. Instantaneous strain was measured by following ink marks with a video extensometer. Three samples were tested for each type of design as described previously in Table 1.

1.3.2. Results

Figure 2:
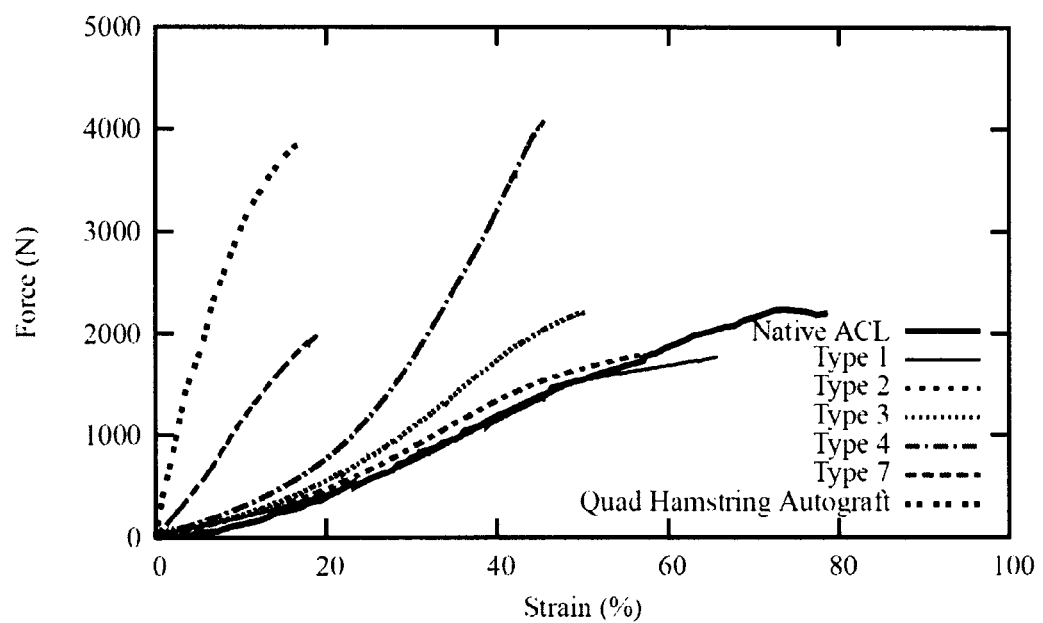
Figure 3:
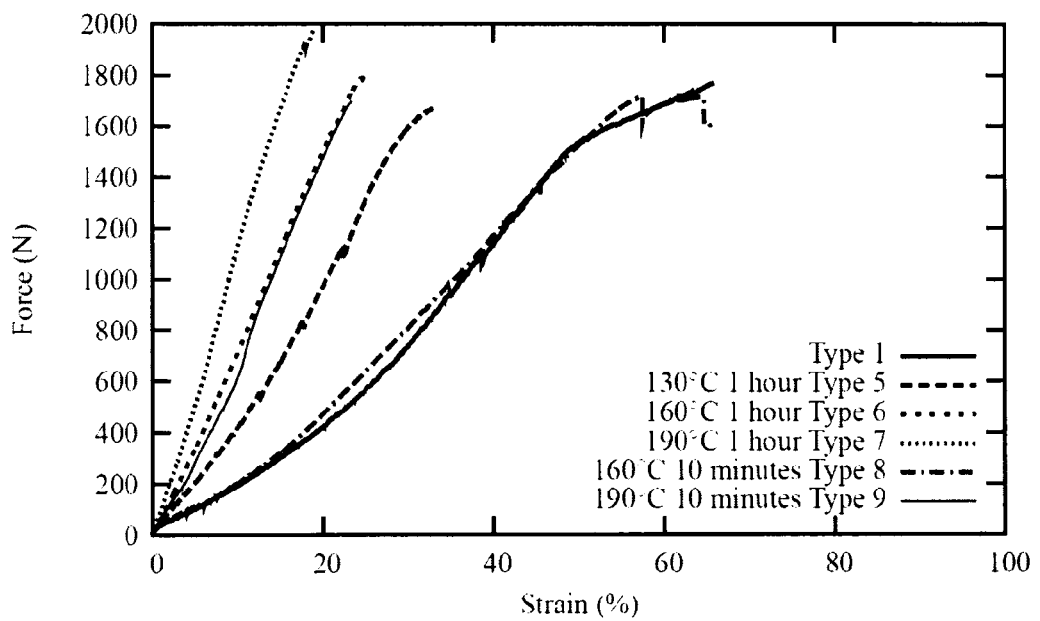
FIG. 3 shows the effect of annealing on the tensile behavior of one type of a device according to the invention.
Figure 4:
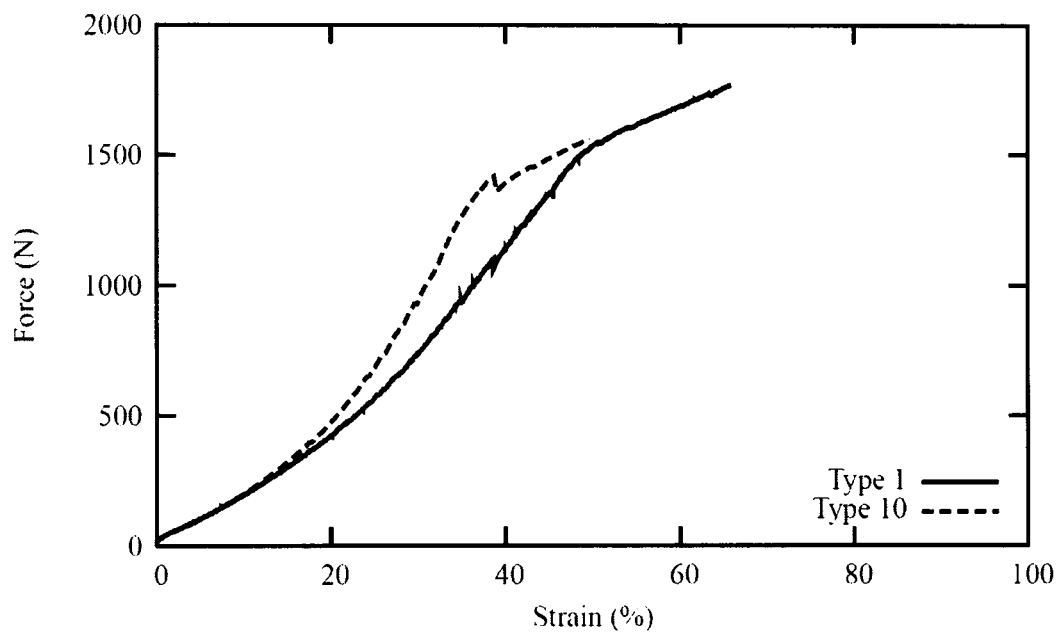
FIG. 4 shows the result for one type of device with and without coating by a hydrogel.

Results are given in FIGS. 2, 3 and 4. FIG. 2 compares the results for type 1, 2, 3, 4, 5 and 7 with literature data showing the tensile behavior of native ACL and hamstring tendon grafts. The behavior of native ACL was reproduced from the results of Woo et al. (Woo S. L. et al. American Journal of Sports Medicine, 1991, 19, p. 217) taking a ligament length of 20 mm to estimate strain from displacement. The behaviour of hamstring tendon grafts was reproduced from the results of Kim D. H. et al. (Kim D. H. et al. American Journal of Sports Medicine, 2003, 31, p. 861.) taking a tendon length of 30 mm to estimate strain from displacement.

All types of device exhibited a non-linear elasticity with a toe region as well as an ultimate strain greater than 15% suitable for low tension and wear during the swing phase of walking. The stiffness of the devices is given by the slope of a linear fit of the load versus strain curves in the 0-10% range. All designs exhibited an acceptable value for stiffness within the range of the currently available ACL replacements. The Type 1 and Type 2 devices had the approximate stiffness of allograft replacements or the native ligament of a middle aged person. The Type 3 device had a stiffness value very close to that of a young person's native ACL. Finally, stiffness could be largely increased with the PVA/UHMWPE structure (Type 4) or in the annealed device (Type 7). They had a stiffness up to about three times greater than that of native ligaments and similar to autografts harvested from the patellar tendon or hamstrings. In the case of the PVA/UHMWPE structure shown here, the high stiffness is obtained after the toe-region (in the 30-40% strain range).

FIG. 3 shows how annealing can be used to tune the tensile behaviour. These results are obtained on a Type 1 structure but similar results are obtained on the other structures. For a given annealing time (1 hour), an increase in the annealing temperature from 130° C. to 190° C. increases the stiffness of the device up to five times (Types 5 to 7). A similar effect is obtained for shorter annealing times as shown with Type 9 (10 min) However, a temperature that is too low and a time that is too short can have limited effect (Type 8).

FIG. 4 shows the tensile behaviour for a fiber assembly coated by a PVA hydrogel and cross-linked with one freezing-thawing cycle (Type 10). In this case, the mechanical response is preserved after coating with a slight increase in stiffness at large deformation.

Tensile strength was measured by dividing the load at break by the initial section of the sample. Here the section is approximated to a disk of diameter 10 mm for Types 1, 2, 5 to 10 and 11 mm for Types 3 and 4. Ultimate tensile strain corresponds to the strain at break. All devices exhibited values of ultimate tensile load (load at break) and ultimate tensile strain that are appropriate for the replacement of ligaments or tendons. Table 2 below compares these mechanical properties derived from FIGS. 2, 3 and 4 with preferred values for the replacement of ACL ligaments as estimated from the literature.

TABLE 2

|  | Ultimate tensile load, N | Tensile strength, MPa | Ultimate tensile strain | Stiffness, N/% |
|---|---|---|---|---|
| Preferred values for ACL replacement | 1100-4000 | 15-50 | >15% | 20 (native ACL) 300 (tendon) |
| Type 1 | 1700 | 22 | 65% | 25 |
| Type 2 | 1750 | 22 | 60% | 40 |
| Type 3 | 2100 | 22 | 50% | 65 |
| Type 4 | 4000 | 42 | 45% | 30 (150)* |
| Type 5 | 1650 | 21 | 35% | 40 |
| Type 6 | 1800 | 23 | 25% | 70 |
| Type 7 | 2000 | 25 | 20% | 120 |
| Type 8 | 1700 | 22 | 55% | 25 |
| Type 9 | 1700 | 22 | 25% | 60 |
| Type 10 | 1550 | 20 | 50% | 25 |

*Stiffness measured in the 30-40% strain range.

The ligaments obtained according to the invention exhibit the unique combination of a tensile behaviour close to that of native ligaments and tendons possibly including a very similar toe-region, a tensile strength greater than 20 MPa corresponding to ultimate tensile loads greater than 1500N and an ultimate tensile strain greater than 15% as well as the biocompatibility of the selected materials (PVA hydrogel and UHMWPE).

EXAMPLE 3

Method of Measuring the Difference in Tensile Modulus Between Median and End Parts Tensile stiffness S is taken as the slope of a linear fit of the force-strain curve in the strain range 0 to 10%. Strain is measured using video extensometry by following markers placed on the sample. It is given by $(L-L_0)/L_0$ where $L_0$ and $L$ are the initial and instantaneous distances between markers, respectively.

All measurements are made in a swollen state: samples are immerged in distilled water for over 12 h prior to testing and are tested less than 5 min after removal from water and pulled at a strain rate of about $10^{-2}$ s$^{-1}$ (1.5 mm s$^{-1}$).

Examples of Manufacturing Processes

For devices wherein the tensile stiffness of the end parts is at least twice as much as that of the median part ($S_{end\ part}/S_{median} > 2$) the fabrication process consists in coating or embedding the ends of a PVA construct made of one PVA bundle composed of 15 twisted PVA threads themselves composed of 15 twisted fibers with a 15 wt % PVA aqueous solution by dipping and physically cross-linking the solution by drying.

Results as follows:

With no treatment $S_{median} = 0.4$ N/%

With coating+drying treatment $S_{end\ part} = 1.4$ N/% $> 2$ $S_{median}$

For devices wherein the tensile stiffness of the end parts is at least five times as much as that of the median part ($S_{end\ part}/S_{median} > 5$) the fabrication process consists in coating or embedding the end parts of a PVA construct made of one PVA bundle composed of 15 twisted PVA threads themselves composed of 15 twisted fibers with a 15 wt % PVA aqueous solution by dipping and physically cross-linking the solution by drying followed by local annealing at 150° C. for 1 h.

With no treatment $S_{median} = 0.4$ N/%

With coating+drying+annealing treatment $S_{end\ part} = 6$ N/% $> 5$ $S_{median}$ In order to obtain devices having a different ratio between the tensile modulus of the end parts and that of the median part, other fabrication processes may include the addition of biomineral fillers such as hydroxyapatite to in the hydrogel matrix embedding or coating the end parts, or local annealing of end parts only.

EXAMPLE 4

Method of Measuring the Tensile Behaviour of the Median Part in the Low (0 to 5%) Strain Regime Modulus ($E_{0-5}$) is taken as the slope of a linear fit of the stress-strain curve in the strain range 0 to 5%. Stress is calculated by dividing the tensile force by the initial cross-section area of the median part, $S_0$. Strain is measured using video extensometry by following markers placed on the sample. It is given by $(L-L_0)/L_0$ where $L_0$ and $L$ are the initial and instantaneous distances between markers, respectively.

All measurements are made in a swollen state: samples are immerged in distilled water for over 12 h prior to testing and are tested less than 5 min after removal from water and pulled at a strain rate of about $10^{-2}$ s$^{-1}$ (1.5 mm s$^{-1}$).

Examples of Manufacturing Processes:

Fabrication process for devices having a tensile modulus superior to 1 or 10 MPa in the 0 to 5% strain range.

The process consists in assembling PVA strands in parallel. Each strand being composed of PVA threads, in turn composed of twisted PVA fibers. PVA threads are Solvron® MH675 provided by Nitivy Company Ltd. and have more than 600 dtex. Typical median part is composed of 16 parallel PVA strands.

Diameter: 9.5 mm
Cross-Section area: 71 mm$^2$
Tensile modulus in the 0-5% strain range is: 20 MPa Another fabrication process consists in an assembly of a central core composed of PVA strands to form an outside structure wrapping a central core composed of braided PVA and UHMWPE strands.

Diameter: 10 mm
Cross-Section area: 78 mm$^2$
Tensile modulus in the 0-5% strain range is: 27 MPa Fabrication process for devices having a tensile modulus superior to 40 MPa in the 0 to 5% strain range.

The fabrication process consists in assembling PVA strands in parallel like indicated above and achieving an annealing of 130° C. for 1 h under tension. Typical median part is composed of 16 parallel PVA strands.

Diameter: 8.5 mm
Cross-Section area: 57 mm$^2$
Tensile modulus in the 0-5% strain range is: 68 MPa Fabrication process for devices having a tensile modulus superior to 100 MPa in the 0 to 5% strain range.

Same process as above with annealing at higher temperature: 160° C. for 1 h. As above, the median part consists in 16PVA strands in parallel.

Diameter: 8.2 mm.
Cross-Section area: 53 mm$^2$
Tensile modulus in the 0-5% strain range is: 126 MPa Fabrication process for devices having a tensile modulus superior to 150 MPa in the 0 to 5% strain range.

Same process as above with annealing at higher temperature: 190° C. for 1 h. As above, the median part consists in 16PVA strands in parallel.

Diameter: 8.5 mm
Cross-Section area: 57 mm$^2$
Tensile modulus in the 0-5% strain range is: 174 MPa Alternative fabrication processes include the assembly in different appropriate proportions of parallel PVA fibers (in the form of fibers, threads or strands) and high modulus fibers such as UHMWPE, silk, Kevlar, PET, polyester

EXAMPLE 5

Method of Measuring the Tensile Behaviour of the Median Part in the Larger (10 to 15%) Strain Regime Method:

Same method as for the low strain regime. Here modulus $E_{10-15}$ is taken as the slope of a linear fit of the stress-strain curve in the strain range 10 to 15%.

Examples of Manufacturing Processes:

Fabrication process for devices having a tensile modulus superior to 1 or 10 MPa in the 10 to 15% strain range.

The fabrication process consists in assembling PVA strands in parallel. Each strand being composed of PVA threads, in turn composed of twisted PVA fibers. PVA threads are Solvron® MH675 provided by Nitivy Company Ltd. and have more than 600 dtex.

Typical median part is composed of 16 parallel PVA strands.

Diameter: 9.5 mm
Cross-Section area: 71 mm$^2$
Tensile modulus in the 10-15% strain range is: 30 MPa Fabrication process for devices having a tensile modulus superior to 40 MPa in the 10 to 15% strain range.

The fabrication process consists in an assembly of a central core composed of PVA strands to form an outside structure wrapping a central core composed of braided PVA and UHMWPE strands.

Diameter: 10 mm
Cross-Section area: 78 mm$^2$
Tensile modulus in the 10-15% strain range is: 47 MPa Another fabrication process consists in assembling 16 parallel PVA strands in parallel like described above and achieving an annealing of 130° C. for 1 h under tension.

Diameter: 8.5 mm
Cross-Section area: 57 mm$^2$
Tensile modulus in the 10-15% strain range is: 89 MPa Fabrication process for devices having a tensile modulus superior to 100 MPa in the 10 to 15% strain range.

Same process as above with annealing at higher temperature: 160° C. for 1 h. The median part consists in 16PVA strands in parallel Diameter: 8.2 mm.
Cross-Section area: 53 mm$^2$
Tensile modulus in the 10-15% strain range is: 152 MPa Fabrication process for devices having a tensile modulus superior to 150 MPa in the 10 to 15% strain range.

Same process as above with annealing at higher temperature: 190° C. for 1 h. As above, median part consists in 16PVA strands in parallel Diameter: 8.5 mm
Cross-Section area: 57 mm$^2$
Tensile modulus in the 10-15% strain range is: 191 MPa

EXAMPLE 6

Method of Measuring the Flexural Modulus of the Median Part

Flexural modulus $E_f$ is measured by performing a 3 point-bending test under constant load P (attaching a weight in the middle of the sample), and measuring the corresponding deflection d.

Figure 5:
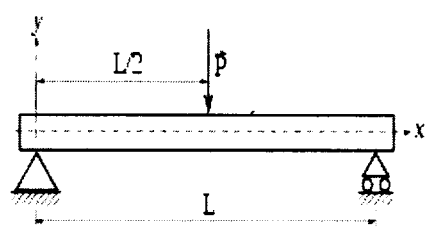
FIG. 5 is relative to the measure of the flexural modulus of the median part.

$E_f$ is then given by:

$$E_f = (L^3/48 I_{Gz}) \cdot (P/d)$$

where $I_{Gz} = b \cdot h^3/12$ for a rectangular cross-section of height h and width b.

or $I_{Gz} = \pi \cdot D^4/64$ for a circular cross-section of diameter D. See FIG. 5.

For braided structures of 12 PVA strands, diameters D of about 8 mm are obtained and the measured flexural modulus is about 15-30 MPa.

A fabrication process for the median part consists in assembling 12 PVA strands in parallel or in a twisted structure. For this case, diameter is D=8 mm and measured flexural modulus is about 8 MPa.

Another fabrication process consists in making a hollow device, using for instance assembly around rod that is removed after assembly. For this type of structure, using 12 twisted PVA strands, diameter is D=8 mm and measured flexural modulus is about 3 MPa.

The invention claimed is:

1. A biocompatible device in the form of an elongated body comprising a flexible median part between two end parts showing a different tensile stiffness from that of the median part, said body having a fibrous structure formed from biocompatible hydrogel forming fibers, said hydrogel forming fibers forming the body of the device, wherein the body is partly or totally coated or entrapped in a hydrogel matrix.

2. The device according to claim 1, wherein the two end parts show a higher tensile stiffness than that of the flexible median part.

3. The device according to claim 1, wherein the two end parts show a higher bending stiffness than that of the flexible median part.

4. The device according to claim 1, wherein the median part shows an ultimate tensile strain greater than 6%.

5. The device according to claim 1, wherein the two end parts show a tensile stiffness that is from 10% to 100 times higher, than that of the flexible median part.

6. The device according to claim 1, wherein the end parts are placed adjacently to each of the ends of the median part and are made of swellable and porous braided, twisted, woven or knitted sections.

7. The device according to claim 1, wherein the flexible median part has a nonlinear elasticity.

8. The device according to claim 1, wherein the median part whose tension stress-strain curve shows a low stiffness region at the lowest levels of tensile strain and a higher stiffness region at greater levels of strain.

9. The device according to claim 1, wherein the flexible median part shows in the 0 to 5% strain range a tensile modulus of 1 to 500 MPa.

10. The device according to claim 1, wherein the flexible median part shows in a 10 to 15% strain range a tensile modulus 1 to 500 MPa.

11. The device according to claim 1, wherein the median part shows in a 10 to 15% strain range a tensile stiffness comprised from about 10 to 500 N/%.

12. The device according to claim 1, wherein the median part shows a flexural modulus from 0.1 to 200 MPa.

13. The device according to claim 1, wherein the fibers and or threads are continuous.

14. The device according to claim 1, wherein the end parts are made of tubular braided, twisted, woven or knitted sections that contain at least one osseointegration promoting substance and/or the device has holes at each end of a tubular section or on a side of the tubular section to allow injection of materials into the space inside the tubular section.

15. The device according to claim 6, wherein the end parts are coated or impregnated with one or several osseointegration-promoting substances.

16. The device according to claim 1, wherein the hydrogel forming fibers are made of polyvinyl alcohol.

17. The device according to claim 1, wherein the hydrogel forming fibers are made of polyvinyl alcohol having a water absorption higher than 10% in weight.

18. The device according to claim 1, further comprising other types of biocompatible fibers assembled with the hydrogel forming fibers.

19. The device according to claim 18, further comprising biocompatible fibers selected from the group consisting of Polyethylene (PE), Poly-L-lactic acid (PLLA), Poly-G-lactic acid (PGLA), Poly-caprolactone (PCL), Silk, Polyesters, Polyethylene terephtalate (PET), Polytetrafluoroethylene (PTFE), PLGA, and Ti wires fibers assembled with the hydrogel forming fibers.

20. The device according to claim 1, further comprising at least one end part an anchoring system selected from the group consisting of a hook, a screw, a buckle, a bone anchor, an interference screw, a cross pin, a suture button, and an eye spliced at said end.

21. The device according to claim 1, wherein at least one of the end parts is filled with a substance, selected from the group consisting of bone mulch, bone cement, and a mineral filler.

22. The device according to claim 1, wherein the hydrogel forming fibers forming the body of the device can be cross-linked.

23. A process for preparing a device according to claim 1 comprising the following steps:
    a) assembly of fibers to form the body,
    b) impregnation of impregnating the fibers, the assembly of fibers or a part or the whole body of the device in a solution of hydrogel-forming polymer or a solution of monomer or oligomer to coat said fibers, or said strands or said assembly of fibers or said body or to embed them in a hydrogel matrix, followed in the case of a wherein impregnating with the solution of monomer or oligomer being followed by a polymerization step,
    c) physical or chemical cross-linking the hydrogel coating, the hydrogel forming fibers or the hydrogel matrix of a part or the whole body of the device.

24. The process according to claim 23 wherein the hydrogel-forming polymer is polyvinyl alcohol and polyvinyl alcohol fibers are used step c) comprises a physical cross-linking step selected from a series of freezing/thawing cycles and/or drying/rehydrating cycles and/or a chemical cross-linking step preferably using irradiation and/or a dialdehyde cross-linker preferably glutaraldehyde.

25. The process according to claim 23 further comprising an annealing step at a temperature near the melting point of the hydrogel forming fibers, before or after step c) of a part or the whole body of the device.

26. A method for inserting a device comprising the following steps:
    a) providing a device according to claim 1,
    b) inserting the device in he a replacement site
    c) attaching a first end part of said device to a first attachment site
    d) optionally, pretensioning the device
    e) attaching a second end part of the device to a second attachment site.

* * * * *